(12) United States Patent
Karell

(10) Patent No.: US 6,408,851 B1
(45) Date of Patent: Jun. 25, 2002

(54) METHOD AND DEVICE FOR HOLDING A TONGUE IN A FORWARD POSITION

(76) Inventor: Manuel L. Karell, 3573-22 St., San Francisco, CA (US) 94114

( * ) Notice: Subject to any disclaimer, the term of this patent is extended or adjusted under 35 U.S.C. 154(b) by 0 days.

(21) Appl. No.: 09/411,349

(22) Filed: Oct. 1, 1999

(51) Int. Cl.[7] .................................................. A61F 5/56

(52) U.S. Cl. ........................ 128/848; 128/859; 602/902

(58) Field of Search ................................. 128/846, 848, 128/859–862; 602/902

(56) References Cited

U.S. PATENT DOCUMENTS

| | | | | |
|---|---|---|---|---|
| 725,354 A | * | 4/1903 | Nicholls | 128/860 |
| 3,522,805 A | * | 8/1970 | Wallshein | 128/860 |
| 4,198,967 A | * | 4/1980 | Dror | 128/860 |
| 4,304,227 A | | 12/1981 | Samelson | |
| 5,649,540 A | * | 7/1997 | Alvarez | 128/860 |
| 5,791,067 A | | 8/1998 | Karell | |

* cited by examiner

Primary Examiner—Michael A. Brown

(57) ABSTRACT

A device and method for pulling a tongue forward thereby preventing obstruction to the flow of air during sleep or an emergency.

14 Claims, 9 Drawing Sheets

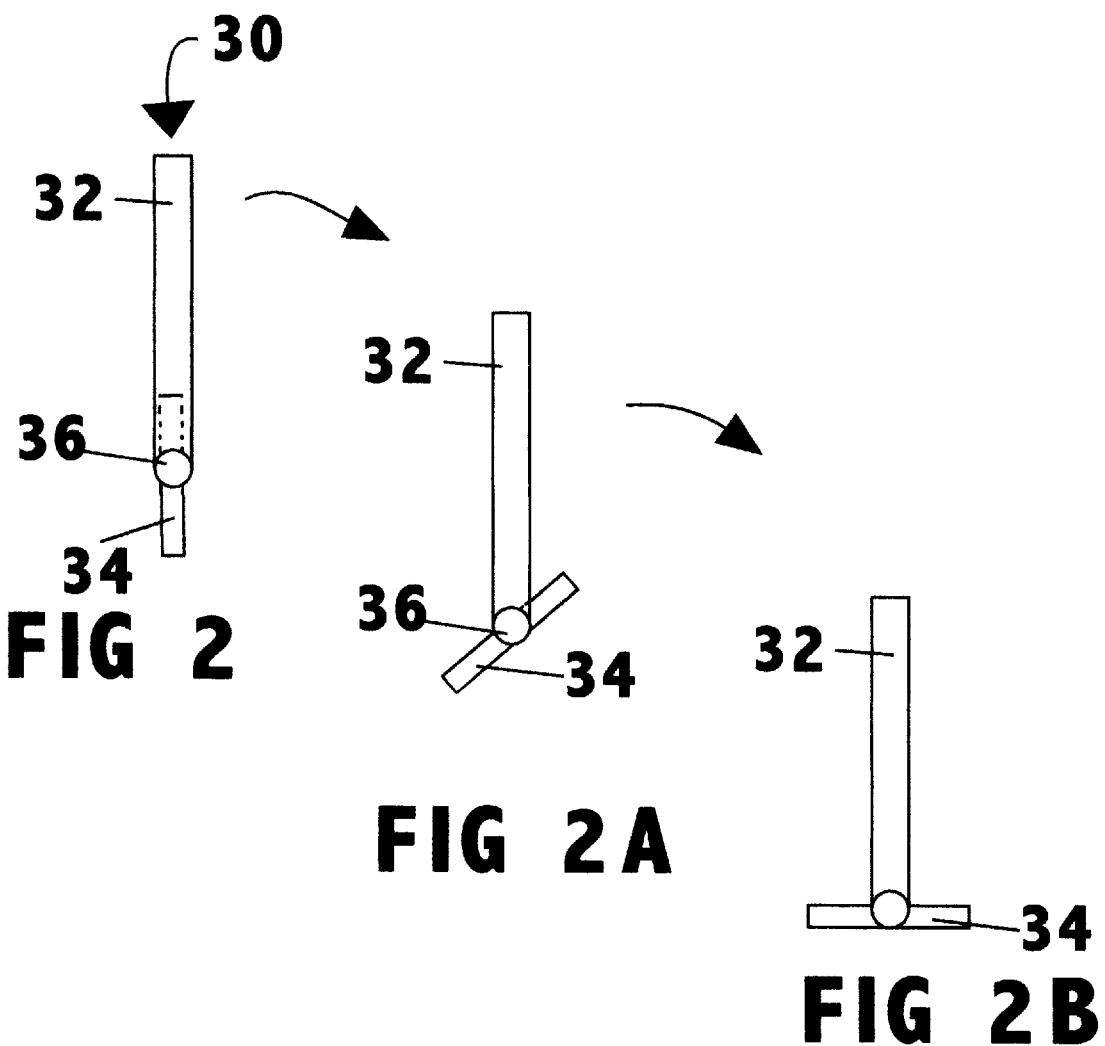

METHOD AND DEVICE FOR HOLDING A TONGUE IN A FORWARD POSITION

FIELD OF INVENTION

This invention relates to a device that decreases interference of breathing during sleep. More particularly, this invention relates to a device that the user can insert into their mouth that alleviates snoring and obstructive sleep apnea.

BACKGROUND OF THE INVENTION

Snoring sounds are vibrations as air passes collapsed structures caused by the relaxation of body tissues during sleep. The tissues which collapses are especially in the lingual compartment, including the tongue, the pharyngeal folds, the soft palate, the muscles of the uvula, and the palate-pharyngeal arch, the pharynx, and the larynx. Muscle tone during normal waking hours maintains the airway patent for free passage of air. Obstructive sleep apnea (OSA) and obstructive breathing (snoring) are mainly caused by the collapse of the airway, especially when the soft palate relaxes while the tongue falls to the back of the throat, both blocking the airway. In OSA, the airway becomes intermittently blocked by the tongue and other airway structures, and at times the person or animal cannot breathe at all.

Uvulopalatopharnygoplasty, adenoidectomy, tonsillectomy, orthognathic, genioglossus advancement, hyoid suspension, lingual plasty, lingual reduction, and other surgery of the mouth, pharynx, hypopharynx and tongue are used for correcting sleep disorders such as OSA or snoring. A need exists for a simple and convenient method and apparatus to obviate surgery while providing a means to bring the tongue forward.

DESCRIPTION OF PRIOR ART

Various devices for preventing or decreasing snoring are known in the prior art. For example, Samelson, in U.S. Pat. No. 4,304,277, discloses a device providing a rearwardly open central socket that cooperates with the forward portion of a user's tongue in such a manner as to draw the tongue forward to increase the unobstructed dimension of the breathing passage. The tongue is held in the socket by negative pressure developed in the socket. The tongue thus held draws the body of the tongue forward thereby increasing the dimension of the air flow passage to facilitate breathing.

Karell in U.S. Pat. No. 5,792,067 discloses a means to reduce or prevent snoring and OSA by increasing muscle tone to airway structures (muscles) by applying electrical energy through strategically placed electrodes within a removable dental appliance. Karell discloses an intraoral structural support containing electrodes for making contact with intraoral mucosa. Energizing the electrodes with electrical energy causes stimulation to nerves and muscles, which in turn causes increased muscle tone and muscle contraction.

The present invention provides a method and device that can prevent snoring and OSA. The device can be adjusted and form fitted by the user, is of simple design, and may be more comfortable than the devices disclosed by the prior art.

One object of the present invention and method is to provide an anti-snore or anti-OSA device that serves to hold the tongue in a forward position, thereby drawing the remainder of the tongue forwardly to increase airway passage.

A further object of the present invention is to provide an anti-snore or anti-OSA device that provides an airway within the appliance. Also, the airway has the capability for attaching to other medical equipment such an an ambu bag or other airway means, including oxygen delivery, respiratory and CPAP systems.

A further object of the present invention is to provide an anti-snore or anti-OSA device that provides one or more electrodes for making contact to intraoral structures for increasing muscle tone by the application of energy from an energy source.

Another object of the present invention is to provide an anti-snoring or anti-OSA device which is moldable after immersion in boiling water or some other method of molding, so that it can be adapted by the user to have a comfortable and individualized fit.

And still another object of this invention and method is to provide an anti-snore device which also prevents bruxism (nocturnal tooth grinding), by bringing the tongue forward through the teeth.

And still another object is provide for a configuration allowing for unity of construction thereby having no parts which may be swallowed.

And still another object is to provide for a configuration allowing for emergency airway usage.

And still another object is to provide a simple method for keeping a tongue forward during sleep and at other times.

These and other objects and advantages of the invention will become clear from the following description of a preferred embodiment of the invention.

SUMMARY OF THE INVENTION

A device of the instant invention can be readily adapted to fit any particular user's mouth, human or animal, for the prevention of bruxism, snoring, other obstructed breathing problems such as OSA, and may be fitted and adjusted by the user. In general, the method for reducing interference of breathing during sleep comprises the following steps: (a)making a hole in a user's tongue; (b)molding an structural support to a user's mouth; (c)wherein the structural support comprises a releasable fastener; (d)placing the releasable fastener through the tongue hole thereby affixing tongue to structural support, pulling tongue forward and preventing obstruction to the flow of air. The device of the instant invention utilizing this method comprises a structural support for fitting within a user's mouth. Additionally, it comprises releasable fastener for holding the tongue in a forward position. A hole tongue may be made using various implements known in the art. The structural support may be a moldable material that contains the impressions of all or part of the upper and/or lower teeth or gums of a user. The releasable fastener may be a firm or non-firm structure passing through the tongue, as do body piercing tongue rings/posts/bars and strings. Prior to going to sleep, the user inserts the device into his or her mouth, passes the releasable fastener through the tongue, and affixes the tongue to the appliance. In this manner, the forward portion of the tongue is held firmly in position to, as example, the rear of the incisor teeth region, thereby pulling the entire tongue forward, thereby opening the airway. The releasable fastener may simply be a hook. Or it may be a pivoting bar which after passing through the tongue, pivots to become a substantially perpendicular "T" shape for comfortably resting under the tongue (that is, the sublingual region of the tongue). The releasable fastener may additionally have a piercer for piercing through a tongue when no previous hole was made.

Although the preferred configuration would be a one-piece device, fastener may be separate from the structural support. An example of such a configuration is one in which a hook-and-eye arrangement is utilized, wherein, for example, the structural support has the hook and the fastening means has the eye. There are many coupling systems are known to the art; for example, the structural support may contain a magnet and another magnet may be inserted through the tongue, or a screw threaded coupling may be utilized.

A simpler method for reducing interference of breathing during sleep may be to place a bar through a forward portion of a tongue so that during sleep the bar can be positioned external to a user's teeth for keeping the tongue in a forward position.

The device may additionally have an airway and/or electrodes. U.S. Pat. No. 5,792,067 to Karell is disclosed and is incorporated herein by reference. This patent teaches a device and method and provides appropriate techniques and devices amenable to the practice of the instant invention.

The device may be configured for use in emergency situations in which case the structural support is configured as an airway with a stop. In this configuration the releasable fastener contains a sharp piercer for piercing through a tongue which has no previous hole. Also, the airway has the ability for attaching to an ambu bag and other airway devices, including oxygen delivery, respiratory and CPAP systems.

BRIEF DESCRIPTION OF THE DRAWINGS

The method and device of the invention will become more apparent from the ensuing description when considered together with the accompanying drawings wherein:

FIGS. 2, 2A, 2B are views illustrating a releasable fastener having pivoting capability for becoming substantially perpendicular and for being placed sublingually.

Figure 1:
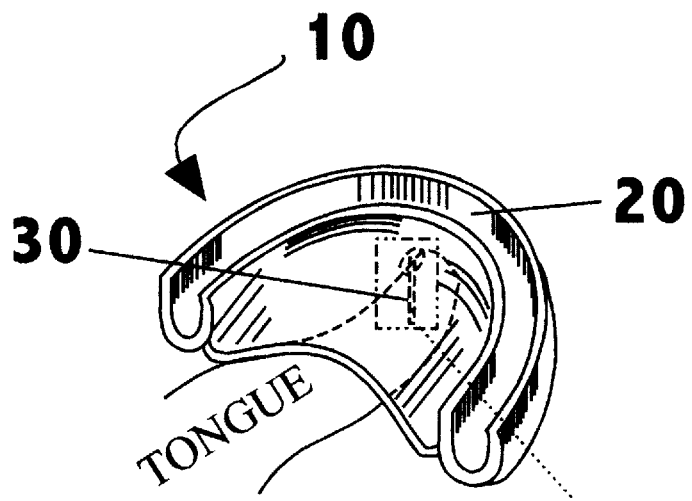
FIG. 1 is a simplified plano-perspective view illustrating the method and device for holding a tongue in a forward position illustrating the instant invention having a structural support with a releasable fastener.

REFERENCE NUMBERS 10 instant invention generally
20 support structure
20' support structure configured to fit between teeth
30 releasable holder
30' releasable holder configured as hook
32 component of releasable holder configured with a pivoting bar
34 pivoting bar of releasable holder
36 pivoting mechanism of releasable holder
40 airway
42 internal opening of airway
44 electrodes
46 wires attached to electrodes
52 stop
54 piercer
56 piercer end region having flange
60 releasable holder coupler configured as hook in "hook-and-eye"
62 releasable holder coupler passing through tongue configured as eye in "hook-and-eye"
70 releasable holder coupler configured with magnet for "magnet coupler"
72 releasable holder coupler passing through tongue configured as magnet for "magnet coupler"
80 releasable holder having no support structure
90 releasable holder having bifurcating bar

DETAILED DESCRIPTION OF THE INVENTION

The instant invention is generally referred to as 10 in FIG. 1, having a structural support 20 and a releasable fastener 30. The structural support 20 may be molded to a user's teeth and is for insertion into the user's mouth. The releasable fastener 30 is passed through the tongue for releasably affixing the tongue to the support means and for holding the tongue in a forward position in the mouth. Therefore, the tongue is not permitted to flop backward during sleep and to obstruct air passage.

Figure 1A:
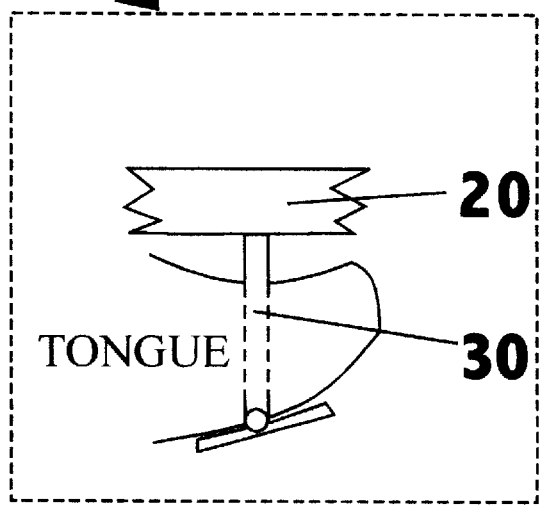
FIG. 1A is an enlarged view of a section of the instant invention illustrating how the releasable fastener passes through the tongue.

FIG. 1A is a section of the device enlarged to illustrate how the releasable fastener 30 passes through the tongue.

In FIGS. 1 and 1A, the structural support is configured to enclose the upper teeth allowing for the releasable fastener 30 to be positioned downward into the mouth and superior to the tongue. FIG. 1A additionally illustrates that a portion of the releasable fastener 30 rests under tongue. FIGS. 2, 2A, 2B shows a releasable fastener 30 further having a pivot 36 and a bar 34 which becomes positioned substantially perpendicularly under the tongue, that is, to the sublingual side of the tongue. The above configuration allows for unity of construction thereby having no components that may be swallowed.

Figure 3:
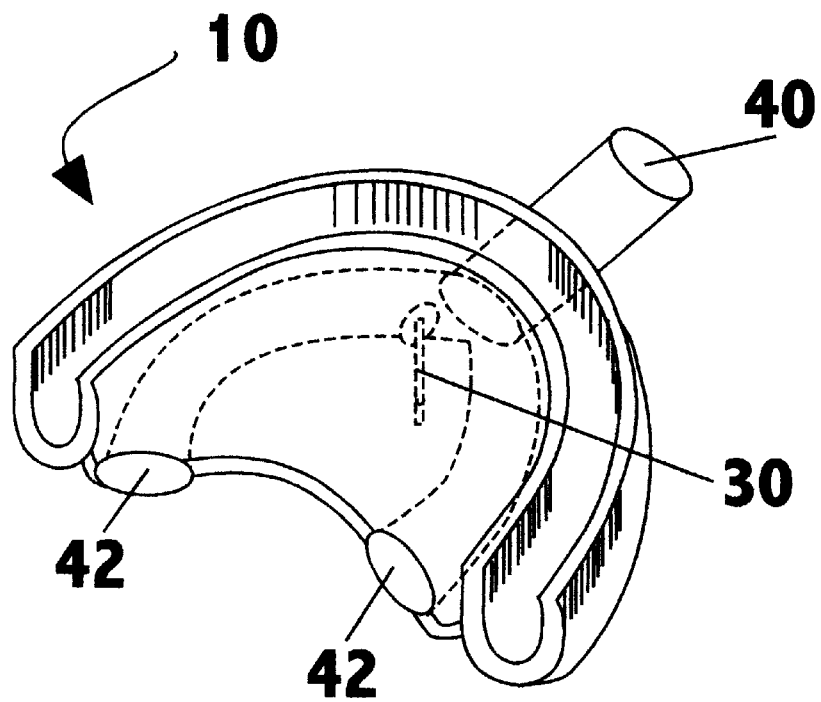
FIG. 3 illustrates the instant invention additionally having an airway.

In FIG. 3 the instant invention 10 additionally has an airway 40 which protrudes outside mouth and having two or more internal openings 42.

Figure 4:
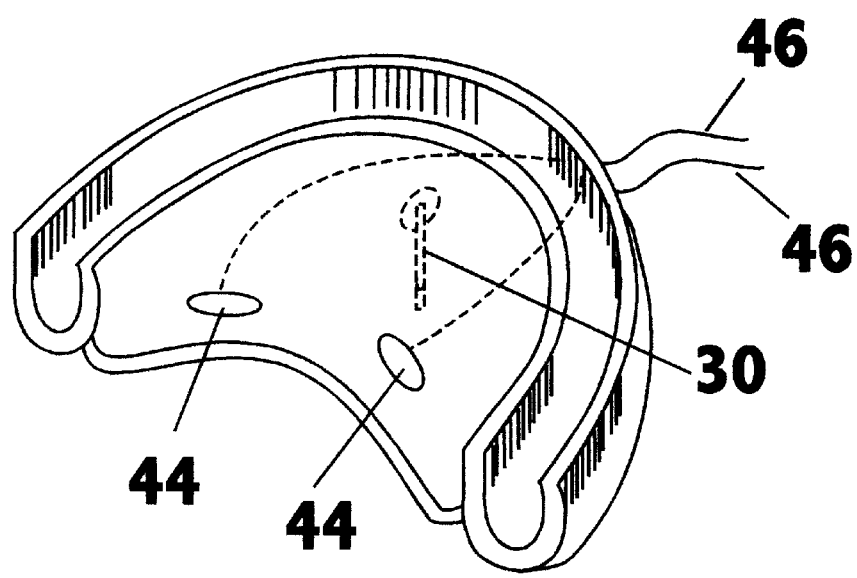
FIG. 4 illustrates the instant invention additionally having electrodes and wires for attaching to an energy source.

In FIG. 4 the instant invention 10 additionally has electrodes which connect to wires 46 protruding external to the mouth for connecting to an energy source (not shown).

Figure 5:
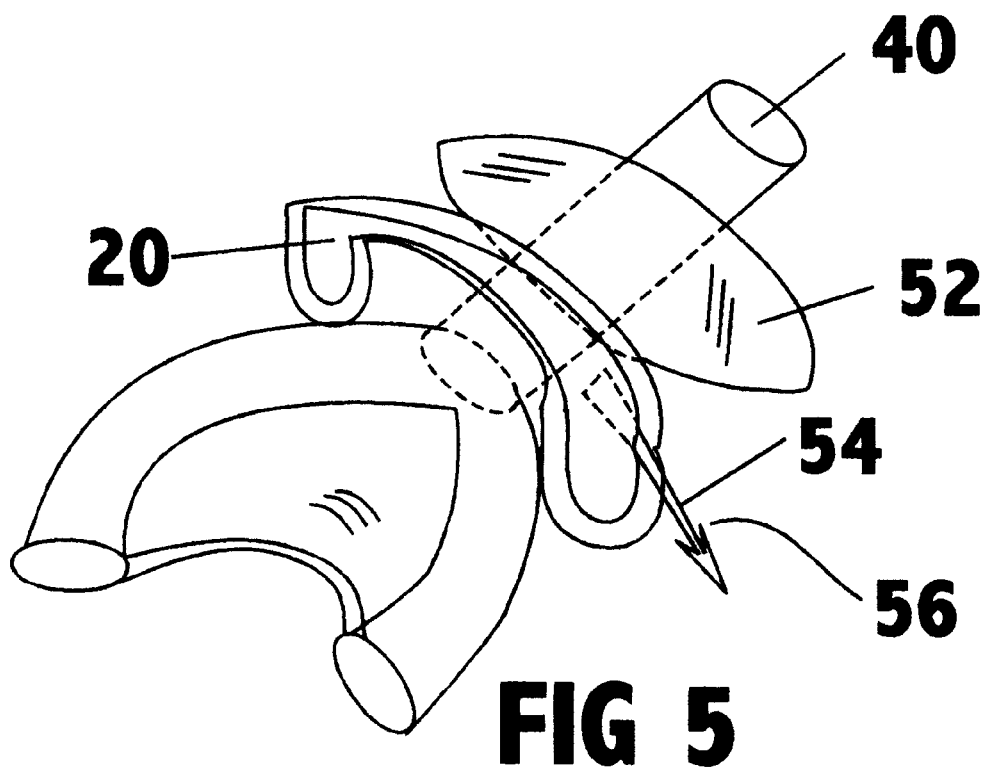
FIG. 5 illustrates the instant invention configured for use in emergency situations having a tongue piercer.

In FIG. 5 the instant invention additionally comprises a stop 52 which is operationally connected to the airway 40. The stop 52 prevents the device from entering the mouth. In this configuration, the structural support 20 is configured to partially enclose the upper teeth. The structural support 20 additionally has a tongue piercer 54. The tongue piercer 54 is stabbed through the tongue and remains positioned because of flange 56 sublingually.

Figure 6:
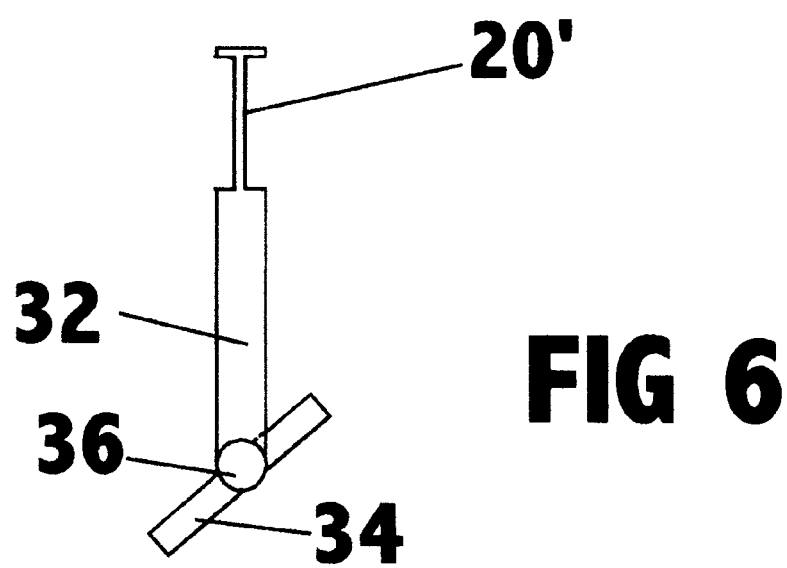
FIG. 6 illustrates the instant invention having a support structure configured to fit between teeth.

In FIG. 6 the instant invention is configured wherein the structural support 20' is placed between teeth. This configuration allows for the smallest device.

Figure 7:
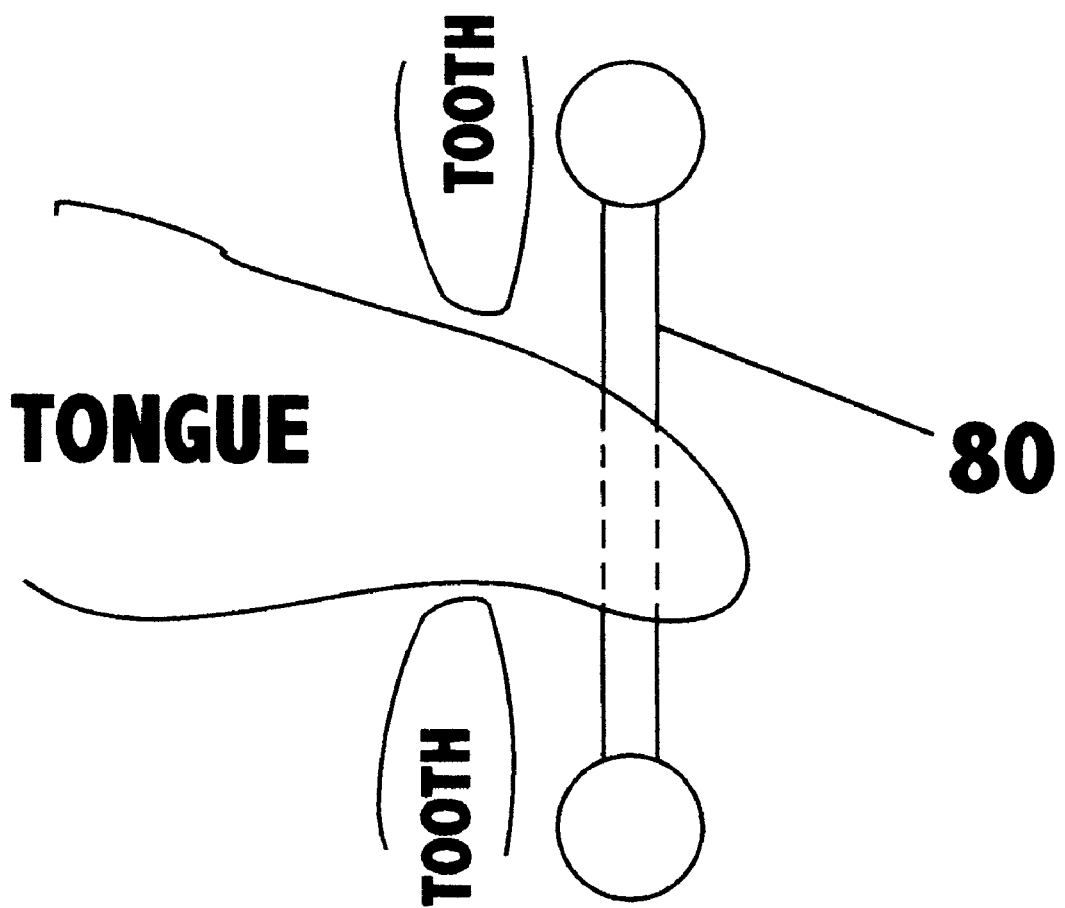
FIG. 7 illustrates the method of holding a tongue in a forward position utilizing a bar inserted through the tongue and held external to teeth.

In FIG. 7 a method for holding a tongue in a forward position is illustrated. A bar 80 is inserted through the tongue and is positioned external to teeth, thus holding tongue in a forward position. A user wishing to reduce interference during sleep would insert the bar 80 through a forward portion of the user's tongue. The bar is then placed external to the teeth, thereby pulling and holding the tongue in a forward position reducing interference of airway passage during sleep.

Figure 8:
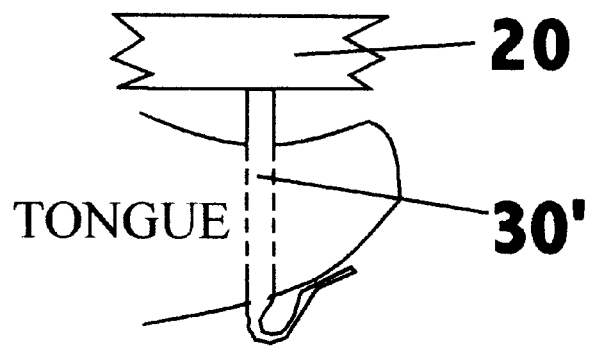
FIG. 8 illustrates a releasable fastener configured as a hook for holding the tongue.

In FIG. 8 the releasable holder 30' is configured to be in a shape of a hook, wherein the distal portion of the hook is flexible to allow for insertion through the tongue.

Figure 9:
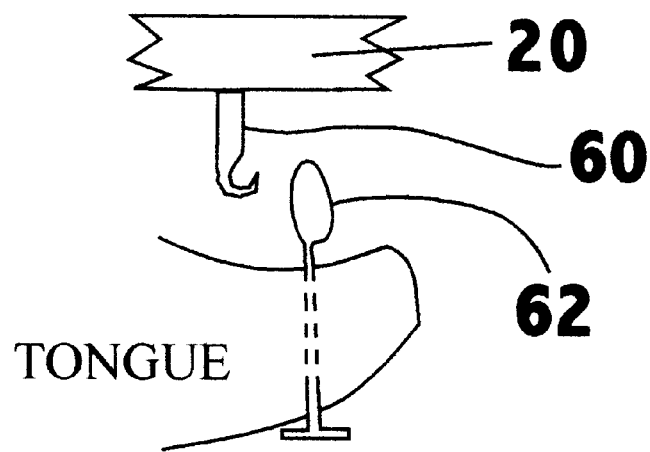
FIG. 9 illustrates the releasable fastener configured as a "hook" for coupling with an "eye" inserted through the tongue (hook-and-eye coupler).

In FIG. 9 the releasable holder 60 is configured to be in a shape of a hook, for coupling with an eye 62 wherein the coupling method is "hook-and-eye" and the releasable holder is of two individual components.

Figure 10:
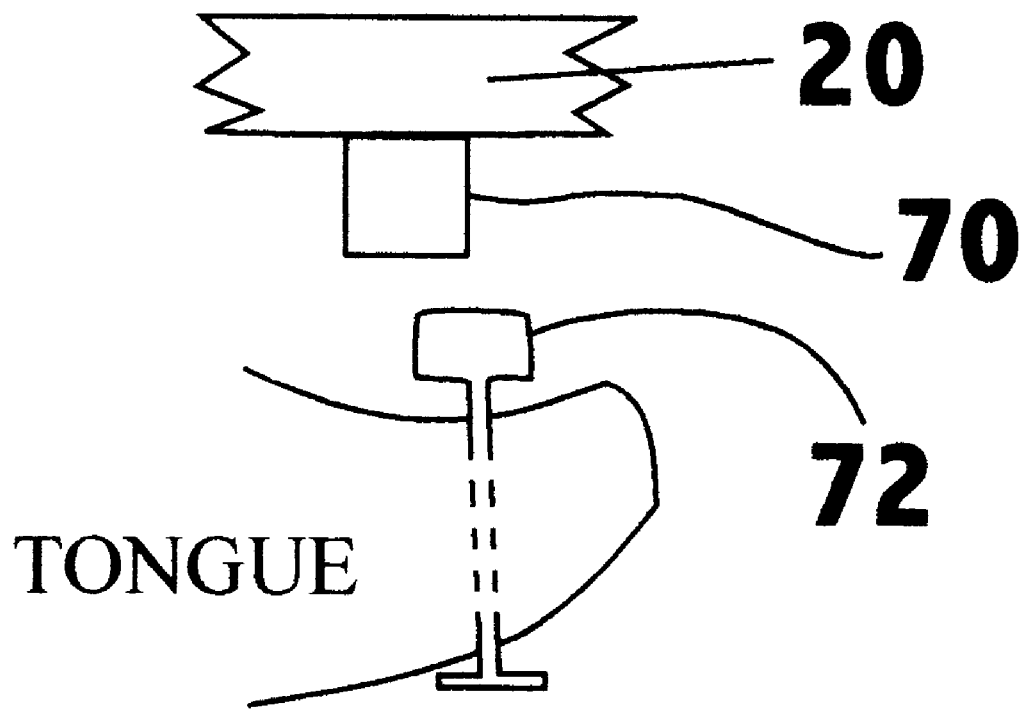
FIG. 10 illustrates the releasable fastener configured with a magnet for coupling to another magnet inserted through tongue (magnet to magnet coupler).

FIG. 10 the releasable holder 70 is configured to have a magnet for coupling with another magnet 72 wherein the coupling method is magnet to magnet and the releasable holder is of two individual components.

Figure 11:
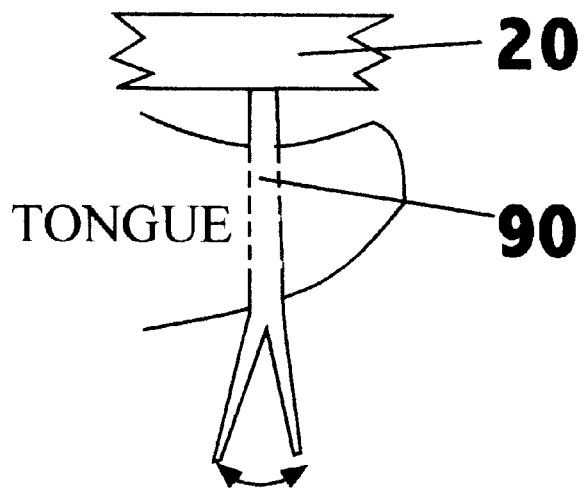
FIGS. 11 and 11A illustrates the releasable fastener configured as a bifurcating bar which bifurcates after passing through the tongue.
Figure 11A:
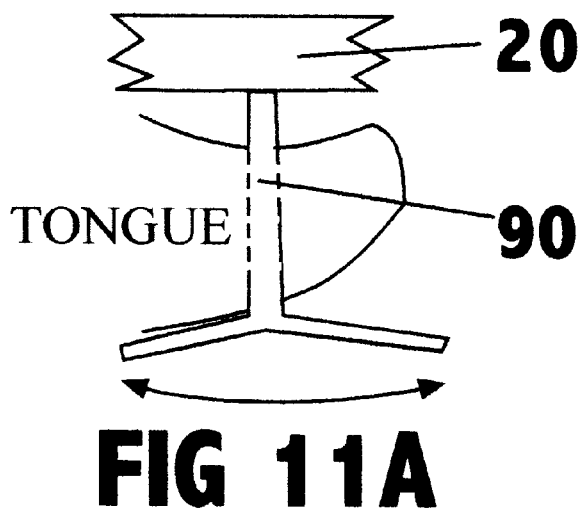

FIGS. 11 and 11A the releasable holder 90 is configured to have a bifurcating bar which bifurcates after passing through the tongue.

Figure 12:
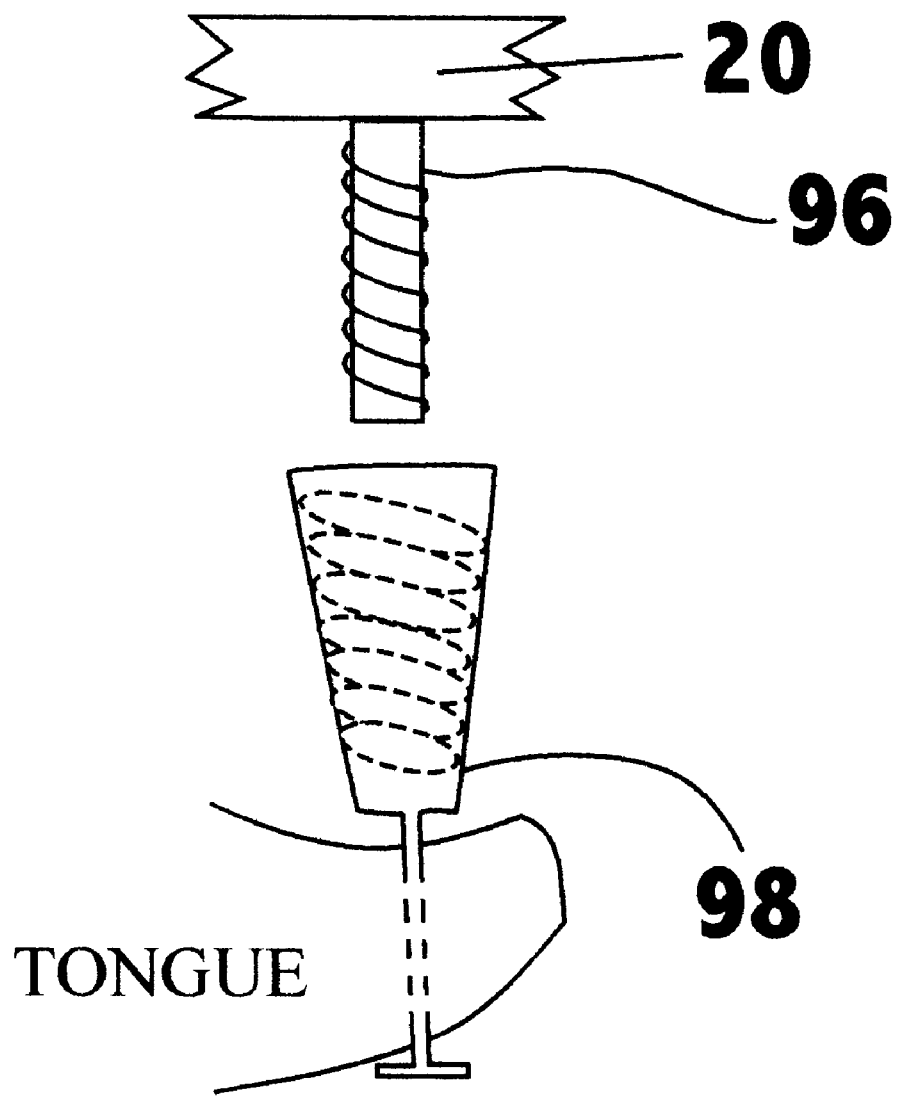
FIG. 12 illustrates the releasable holder having a threaded component and a screw.

FIG. 12 the reasable holder 94 and 96 is composed of two threaded components which screw together.

The present invention may be embodied in other specific forms without departing from the spirit or essential attributes thereof and, accordingly, reference should be made to the appended claims, rather than to the foregoing specification as indicating the scope of the invention.

What is claimed is:

1. A device for reducing interference of breathing or bruxism by holding a tongue in a forward position comprising a structural support means having a configuration that is adapted for insertion into a user's mouth, an attachment means attached directly to said structural support, said attachment means includes a vertical member extending from said structural support and a bar attached to said vertical member by a horizontal pivot mechanism which permits to the bar to be inserted in the tongue, than rotated from a vertical position to a horizontal position so the bar can be locked against the lower surface of the user's tongue.

2. The device of claim 1 wherein said structural support means further comprises an airway means for providing air exchange between the user's and ambient air.

3. The device of claim 1 wherein said structural support means further comprises at least one electrode connected to an energy source, wherein said electrode make contact to intraoral structures for increasing muscle tone and muscle contraction.

4. The device of claim 1 wherein said attachment means further comprises a tongue piercing means for piercing a hole in user's tongue.

5. The device of claim 1 wherein the attachment means is a hook.

6. The device of claim 1 wherein the vertical member and the bar is bifurcated so the bar can be pass through the hole and form a perpendicular support.

7. The device of claim 1 wherein the structural support is configured to be placed between teeth.

8. A method for reducing interference of breathing during an emergency comprising the following steps:

inserting an airway into a mouth wherein said airway comprises a releasable fastening means having a piercing means;

piercing a tongue with said piercing means thereby affixing tongue to airway, pulling tongue forward and preventing obstruction to the flow of air.

9. A device for using method claim 8 for reducing interference of breathing comprising:

a structural support means configured for insertion into a user's mouth;

said structural support means comprising an airway means for providing air exchange between the user and ambient air;

said airway means comprising a stop means for preventing the device from wholly entering the mouth;

said structural support means additionally comprising a piercer means for piercing the tongue of the user.

10. A method for reducing interference of breathing during sleep comprising the following step: placing a bar through a forward portion of a tongue so that during sleep the bar is positioned external to a user's dentition for keeping the tongue in a forward position.

11. A device using method of claim 10 for reducing interference of breathing during sleep comprising: a bar inserted through a user's tongue for keeping the tongue in a forward position wherein said bar is placed external to the teeth.

12. A method for reducing interference of breathing by holding a tongue in a forward position comprising the following steps:

making a hole in the tongue of a user;

molding a structural support to fit within a user's mouth wherein the structural support comprises a releasable fastener means;

inserting the releasable fastener means through the hole in the tongue thereby affixing the tongue to the structural support, pulling the tongue forward and reducing interference of breathing.

13. A method of claim 12 wherein said structural support additionally comprises one or more electrodes for making contact with one or more intraoral anatomical structures wherein said electrodes are operably connected to an energizing source for an additional step of energizing said electrodes for increasing muscle tone or causing a muscle contraction of the user.

14. A method of claim 12 wherein said structural support additionally comprises an airway means for an additional step of providing for air to exchange between said user and ambient air.

* * * * *